United States Patent
Norli et al.

(10) Patent No.: US 10,527,590 B2
(45) Date of Patent: Jan. 7, 2020

(54) APPARATUS AND METHOD FOR INSPECTING A PIPELINE

(71) Applicant: HALFWAVE AS, Hovik (NO)

(72) Inventors: Petter Norli, Oslo (NO); Wayne Fleury, Eidsvagneset (NO); Paul Doust, Weymouth Dorset (GB)

(73) Assignee: Halfwave AS, Hovik (NO)

( * ) Notice: Subject to any disclaimer, the term of this patent is extended or adjusted under 35 U.S.C. 154(b) by 0 days.

(21) Appl. No.: 15/552,652

(22) PCT Filed: Feb. 24, 2016

(86) PCT No.: PCT/NO2016/050033
§ 371 (c)(1),
(2) Date: Aug. 22, 2017

(87) PCT Pub. No.: WO2016/137335
PCT Pub. Date: Sep. 1, 2016

(65) Prior Publication Data
US 2018/0017533 A1 Jan. 18, 2018

(30) Foreign Application Priority Data
Feb. 24, 2015 (NO) .................................. 20150256

(51) Int. Cl.
*G01N 29/34* (2006.01)
*G01N 29/26* (2006.01)
(Continued)

(52) U.S. Cl.
CPC ........... *G01N 29/348* (2013.01); *G01N 29/04* (2013.01); *G01N 29/12* (2013.01);
(Continued)

(58) Field of Classification Search
CPC .... G01N 29/12; G01N 29/343; G01N 29/348; G01N 29/04; G01N 29/2437;
(Continued)

(56) References Cited

U.S. PATENT DOCUMENTS 3,916,699 A 11/1975 Moran et al.
4,237,723 A * 12/1980 Kent ................... G01M 3/2846
73/49.6
(Continued)

FOREIGN PATENT DOCUMENTS

GB         2456229      *  1/2009
WO   WO1996013720 A1      5/1996
WO   WO2009038456 A1      3/2009

*Primary Examiner* — Jacques M Saint Surin
(74) *Attorney, Agent, or Firm* — Butler Snow LLP

(57) ABSTRACT

It is described an apparatus for inspecting a pipeline, said apparatus including a cylindrical body (15) adapted to be transported inside said pipeline, an array of acoustical transducers ($T_{x,y}$) installed in the surface of the cylindrical body (15), the acoustical transducers being organized in columns and rows in a belt around the cylindrical body, a controller adapted to initiate a transmission of an acoustical signal from a first transducer ($T_{2,2}$) and a reception of said acoustical signal from other transducers in said array surrounding the first transducer, the controller further being adapted to determine the direction to a flaw in the wall of said pipeline from the received acoustical signals.

6 Claims, 2 Drawing Sheets

(51) Int. Cl.
*G01N 29/12* (2006.01)
*G01N 29/04* (2006.01)
*G01N 29/24* (2006.01)
*G01N 29/44* (2006.01)

(52) U.S. Cl.
CPC ....... *G01N 29/2437* (2013.01); *G01N 29/262* (2013.01); *G01N 29/343* (2013.01); *G01N 29/4409* (2013.01); *G01N 2291/014* (2013.01); *G01N 2291/0234* (2013.01); *G01N 2291/0289* (2013.01); *G01N 2291/044* (2013.01); *G01N 2291/0427* (2013.01); *G01N 2291/103* (2013.01); *G01N 2291/106* (2013.01); *G01N 2291/2636* (2013.01)

(58) Field of Classification Search
CPC ............. G01N 29/4409; G01N 29/262; G01N 2291/0289; G01N 2291/014; G01N 2291/0234; G01N 2291/0427; G01N 2291/044; G01N 2291/103; G01N 2291/106; G01N 2291/2636
USPC .......................................................... 73/628
See application file for complete search history.

(56) References Cited

U.S. PATENT DOCUMENTS

| | | | | |
|---|---|---|---|---|
| 4,289,019 | A * | 9/1981 | Claytor | G01M 3/243 702/51 |
| 5,460,046 | A | 10/1995 | Maltby et al. | |
| 5,587,534 | A * | 12/1996 | McColskey | G01B 17/02 73/592 |
| 6,588,267 | B1 * | 7/2003 | Bradley | G01V 1/523 181/102 |
| 2014/0278193 | A1 | 9/2014 | Breon et al. | |
| 2018/0196005 | A1* | 7/2018 | Fanini | G01N 27/82 |

* cited by examiner

APPARATUS AND METHOD FOR INSPECTING A PIPELINE

FIELD OF THE INVENTION

The present invention relates to the field of non-destructive testing, and more specifically to a pipeline inspection tool for testing the integrity of oil and gas pipelines using acoustical transducers.

BACKGROUND

In the oil and gas industry, there is a need for efficient testing of pipelines. Such pipelines are often difficult to access, e.g. offshore pipelines that may be partly buried, and which forms extended structures. The pipelines are subject to wear from corrosive fluids and sand, and deformation from movements in the seabed. Said pipelines are also prone to developing cracks, in particular in the welding seams. Welding seams are inherent weak points due to the changes in the steel structure caused by the welding process. Cracks may develop due to stress caused by temperature cycling and movements in the seabed.

The structural integrity of pipelines may be tested using inspection pigs which travel inside the pipelines measuring the condition of the pipe wall. There have been devised several methods for measuring the condition of pipeline walls. Here we will mention methods using magnetic flux leakage and ultrasonic testing. Methods using magnetic flux leakage are mainly effective only for detecting metal loss (thinning of the pipeline wall) caused by corrosion. Ultrasonic testing methods are used for detecting corrosion and cracks in pipeline walls, even though there is some overlap between the technologies. Ultrasonic testing using conventional piezoelectric transducers are limited to testing pipelines filled with liquids, as a liquid is needed to conduct the ultrasonic energy into the pipeline wall. The extreme difference in acoustic impedance between air/gas and steel will greatly reduce the amount of acoustic energy being conducted into the pipeline wall in a "dry" pipeline. It has been proposed to use Electro Magnetic Acoustic Transducer (EMAT) technology for testing gas pipelines; this type of transducer generates an electromagnetic field which introduces Shear Horizontal (SH) wave mode ultrasonic waves directly into the pipeline wall. However, such transducers are large, have a limited bandwidth, and must be positioned very close to the pipe wall, preferably less than 1 mm from the wall surface.

From U.S. Pat. No. 8,677,823 there is known a setup wherein a spool carrying acoustical transducers (in an array around the central narrow part of the spool) is sent through a pipeline containing pressurised gas. Acoustic signals are transmitted from each transducer, through the gas medium to the inner surface of the pipe wall.

These are reflected back by the wall and received by the same transducer or by a preselected transducer(s) in the spool. This equipment is used for measuring the diameter of the pipeline to identify deformations to the wall. However, this setup is not suited for testing the material in the wall itself, due to the high impedance contrast between air and steel.

European patent application EP 2 887 060 A1 discloses an apparatus for inspecting pipelines. This application was filed on 20 Dec. 2013, and published on 24 Jun. 2015. The pipe wall is inspected by means of acoustical pulses emitted from an array of transducers, the transducers being localized in a single ring or row around the body of the apparatus, see FIG. 1. The measurements are pulse-echo-measurements, wherein pulses are transmitted and received by the same transducer.

From U.S. Pat. No. 9,852,033 there is known an apparatus for logging oil and gas wells. The apparatus includes a rotating transducer head with three acoustic transducers. The transducer head is rotated while the apparatus is displaced vertically along the well. In this way, the well may be covered by a series of individual measurements covering the wall along a spiral path.

SUMMARY OF THE INVENTION

It is an object of the present invention to provide a device and method for acoustical testing of pipelines that overcomes the above-mentioned problems.

This is achieved in a device and method as defined in the appended claims.

BRIEF DESCRIPTION OF THE DRAWINGS

Further aspects of the invention will appear from the following detailed description when read in connection with the appended drawings, in which.

DETAILED DESCRIPTION

According to the invention, there is provided a device designed as a spool carrying a multi-element array of acoustical transducers, any one of which can be used to transmit or receive acoustic energy at any particular specified time, the device being adapted to be transported through the interior of a pipeline while testing the pipe wall. Such a device is also known as a pig.

Figure 1:
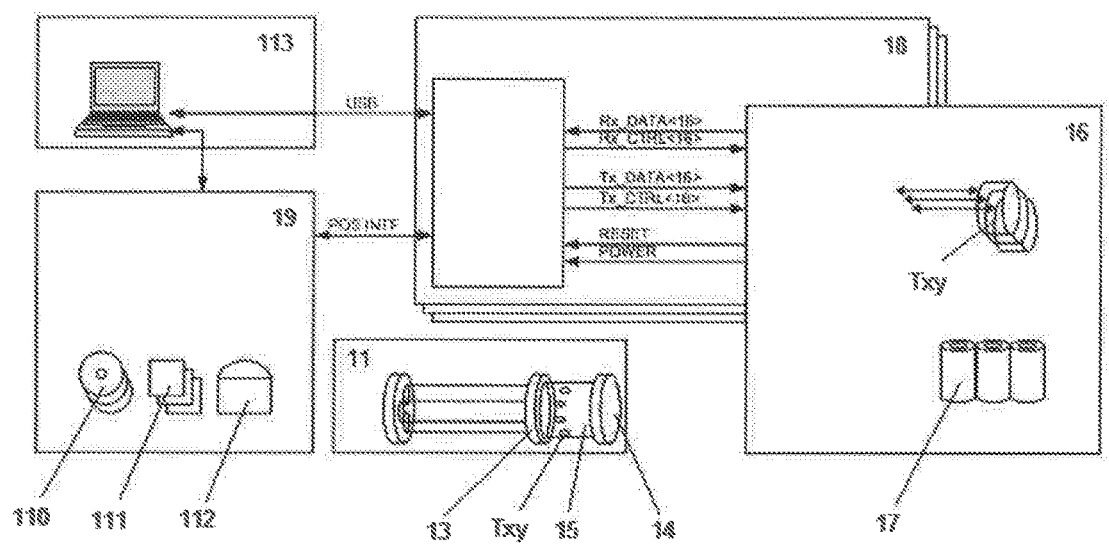
FIG. 1 is a schematic illustration of the inventive device and the electronics circuits of the device.

FIG. 1 shows an embodiment of the inventive device 11, together with electronic modules 16, 18, 19 located inside the device. The device is designed as a spool with two circular end plates 13, 14 joined by a cylindrical body 15, the body being of smaller diameter than the end plates. In the wall of the body 15 there are installed a number of transducers $T_{x,y}$. The transducers are organized in (circular) columns and rows covering a belt around the cylindrical body 15 (only one column shown in the figure). If necessary, each transducer may be composed of several elements in order to obtain sufficient signal strength and a narrow beam.

Inside the body 15 there are electronic circuits for exciting the transducers, receive response signals from the transducers, and store the received signals. The electronic circuits may be organized in several separate modules as shown. An analogue module 16 is carrying the transducers $T_{x,y}$ and a number of batteries 17 powering the entire device. The analogue module 16 is connected to a digital module 18. The digital module 18 includes circuits for controlling the transducers $T_{x,y}$, AD and DA converters, data storage units and a host interface for system configuration and data communication. Further, the device 11 includes a position module 19 supplying position information to the digital module 18. The position module 19 may include odometers 110 in contact with the pipe wall. Here are used three odometers evenly distributed around the circumference of the tool to ensure that at least one of them is in contact with the wall. The odometers will output pulses when the tool is travelling along the pipeline, each pulse indicating that a certain distance has been covered. The pulses will be used to control the firing of the transmitters. Pressure sensors 111 are used to tell the electronics that the tool has been sluiced into a pipeline, whereupon the measuring process will be initiated. There is also included an inductive unit 112, a so-called pig tracker, which will send out low frequency magnetic waves that may be tracked from the outside of the pipeline.

The device may operate in two modes: In "connected mode" the device is connected to a computer 113 for system configuration and retrieval of collected data, whereas in "autonomous mode" the device is operating on its own inside a pipeline without access to the computer. In this mode collected measuring data must be stored on board.

The device is intended to be transported through the pipeline propelled by the differential pressure across the device, while some of the transducers (notably the transducers in one of the columns, such as the transducers $T_{x,2}$, X being 1-n) are fired while the other transducers are listening. However, it should be noted that all transducers may serve as transmitters and receivers, and their role is chosen at will.

As mentioned above, it is an object of the present invention to investigate the properties of the pipeline wall using acoustical transducers, such as piezoelectric transducers, to avoid the drawbacks of EMATs. However, this creates the question of how to obtain an acoustical signal of adequate strength in the wall. Another question is how to decide the correct position of a crack or inhomogeneous structure found in the wall. A third question is how to obtain a sufficient sample point density when the tool is travelling along the pipeline, i.e. how to measure fast enough when the tool is moving at full speed. When transmitting acoustic energy into a pipeline, a reasonably clean signal will initially be received, but later on the signal will be masked by noise created by dispersion effects, etc. This means that there must be an "idle" period of time delay between each transmission. The first and last questions are answered by the particular acoustic pulses used to excite the pipeline wall, while the second question is solved by the particular layout of transducers used in the tool and how they are operated, as will be explained below.

Figure 2:
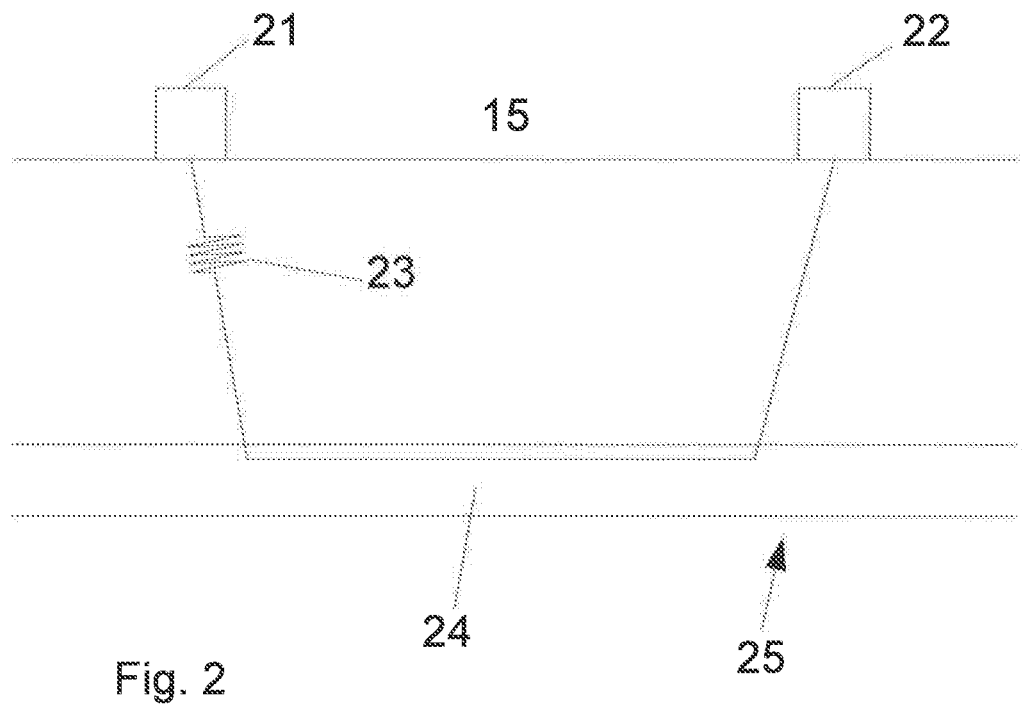
FIG. 2 is a schematic view illustrating the propagation path of acoustical waves between a transmitting and receiving transducer in said inventive device.

FIG. 2 shows the propagation path followed by a signal from a transmitting transducer 21 to a receiving transducer 22. To overcome the impedance barrier between the gas in the pipeline and the wall, the transmitting transducer is transmitting burst pulses 23 at a low frequency. The frequency may be in the range of 200-1400 kHz. This is about ten times lower than in the ultrasonic transducers used in calliper measuring tools. The loss in the gas increases dramatically with frequency. At these low frequencies it has been found favourable to tune the transmitting frequency to a thickness resonance of the wall. This will increase the sensitivity of the measurements, increase the ability to locate a crack and lower the data processing load. Assuming a plane wave at normal incidence, resonance peaks are found at frequencies where the plate thickness is an integer number of half wavelengths. The frequency, f, of a thickness resonance being defined as $f=nc/2D$, c being the acoustical velocity of the wall material, D its thickness and n denoting the harmonic.

The pulses will excite a signal 24 travelling in the wall. This signal is converted back into a compressional wave at the steel/gas interface before impacting the receive transducer 22. Due to the geometrical setup of the transducers, the first arrival detected in the receiving transducer will be a wave that has travelled as a shear mode signal in a part of the trajectory. Later on, signals travelling as Lamb waves will arrive. Lamb waves will have much larger amplitude than shear waves, and this fact may be used to differentiate between the wave types, which all arrive as compressional waves at the receivers.

Figure 3:
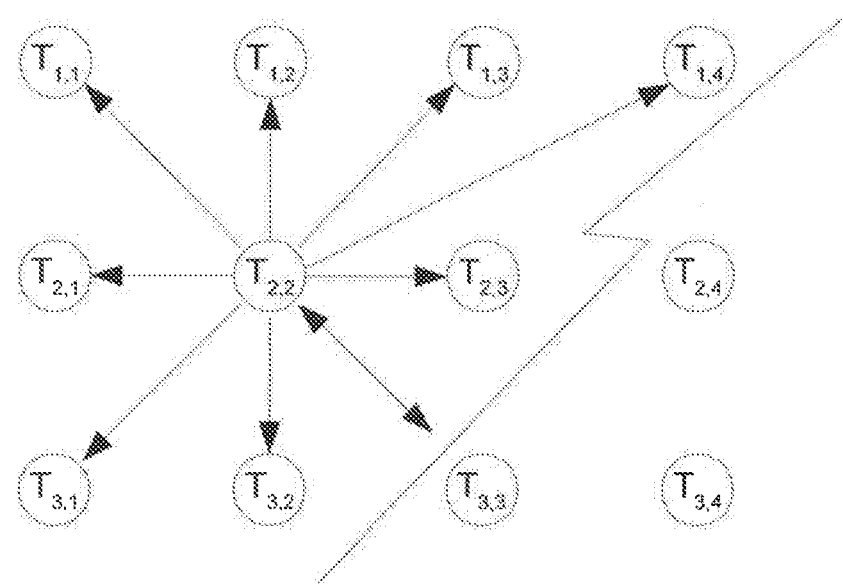
FIG. 3 is a plan view of said propagation path.

FIG. 3 illustrates how the signal from a transducer $T_{2,2}$ may be detected by transducers $T_{1,1}$, $T_{1,2}$, $T_{1,3}$, $T_{1,4}$, $T_{2,1}$, $T_{2,3}$, $T_{3,1}$ and $T_{3,2}$. The signal paths are indicated with arrows. Thus, signals travelling in all directions from the transmitting transducer will be detected. If there is a crack in the wall, transducers located in the "shadow" behind the crack will receive signals with substantially lowered amplitude. This is the case for the transducers $T_{3,3}$, $T_{3,4}$ and $T_{2,4}$, as there is a crack in the path between the transmitter and the receiver which will attenuate the signal. The signal from the transmitter will also be reflected by the crack and arrive at the transducers in front of the crack. However the signal will be inverted in the reflection and this may be used to identify reflected signals. This is indicated with the double headed arrow between the transmitter $T_{2,2}$ and the crack. After firing, the transducer must then listen for inverted reflections. The distance and direction to a crack, or its position, may be found by comparing the signals received by the transducers.

As mentioned above, the transducer is transmitting a signal that is adapted to excite a thickness resonance of the pipe wall. The excitation of the pipe wall may be performed in several ways.

One method is to use a two stage process, in which the transducer first is sending a swept frequency signal (e.g. a chirp) covering a possible thickness resonance frequency of the wall. The thickness of the wall may differ somewhat, and thus the thickness resonance frequency may also be variable as it is determined by the mechanical thickness. When the exact resonance frequency has been determined by analysing the received signal, a second signal on the fixed resonance frequency is transmitted into the pipe wall.

This method may be expanded by letting the sweep cover one or more harmonics of the fundamental resonance. The exact frequency of the resonance may be more accurately determined by measuring the difference in frequency between two frequencies (harmonics) than by counting the fundamental resonance directly.

Further, to speed up the measuring process, several transmitters may be excited simultaneously, each on a different harmonic frequency. Each receiver may receive signals from several transmitters, but may resolve "who is who" by cross correlation with the transmitted signals. In this way several positions on the pipe wall may be investigated simultaneously.

Another method is to excite the pipe wall with a sinc pulse from the transmitter. Thus, the frequency span of the sinc pulses should cover a chosen harmonic of the thickness resonance with some allowance for thickness differences. Also in this case several transmitters may be fired simultaneously on different harmonics of the resonance frequency.

Still another method is to excite the wall using spread spectrum signals. This provides the possibility of coding a number of transmitters differently, i.e. they may transmit simultaneously and the signals may be resolved in the receivers. Each signal may also be tailored to cover a small range of frequencies around a selected harmonic of the wall's thickness resonance, even though this frequency range will not be so narrow and evenly covered as in the two previous embodiments. There are many variations of the spread spectrum technique that may be employed for this purpose, but in particular a direct sequence spread spectrum (DSSS) technique using binary phase shift keying (BPSK) modulation has been found feasible.

The invention claimed is:

1. Apparatus for inspecting a pipeline including: a cylindrical body configured to be transported inside said pipeline, an array of acoustical transducers ($T_{x,y}$) installed in the surface of the cylindrical body, the acoustical transducers being organized in columns and rows in a belt around the cylindrical body, and
- a controller adapted to initiate a transmission of an acoustical signal from a first transducer, the signal exciting a thickness resonance of the pipeline wall travelling in and along the wall, and to initiate a reception of said acoustical signal from other transducers located in said columns and rows, said other transducers surrounding the first transducer, wherein said other transducers detect signals travelling in multiple directions from said first transducer, the controller being further configured to determine the distance and direction to a flaw in the wall of said pipeline by comparing the signals received by said other transducers.

2. A method for testing the wall of a pipeline including the steps of:
- (i) transmitting an acoustical signal from a first transmitting transducer facing the wall and positioned a distance from the wall, the signal exciting a selected thickness resonance frequency of said wall, the signal travelling in and along the wall,
- (ii) receiving an acoustical signal returned from the wall in a number of receiving transducers also facing the wall at a distance from the wall, the receiving transducers being organized in columns and rows and surrounding said transmitting transducer, wherein said other transducers detect signals travelling in multiple directions from said first transducer, and
- (iii) processing the returned acoustical signals to determine the distance and direction to a flaw in the wall of said pipeline by comparing the signals received by said other transducers.

3. A method according to claim 2, wherein the wall is excited by first transmitting a swept frequency signal against the wall, observing any resonances in the received signals, then transmitting a single frequency burst signal against the wall on a selected resonance frequency of the wall from a selected transducer.

4. A method according to claim 2, wherein the wall is excited by first transmitting a sine signal against the wall, the sine signal spanning a range of frequencies covering a chosen harmonic of the resonance frequency.

5. A method according to claim 2, wherein the wall is excited by simultaneously transmitting a second acoustical signal from a second transducer, wherein each transmitting transducer is transmitting on a different harmonic of said resonance frequency.

6. A method according to claim 2, wherein the wall is excited by simultaneously transmitting a second acoustical signal from a second transducer, wherein said first and second acoustical signals are spread spectrum coded signals, wherein each transmitting transducer is coded differently.

* * * * *